(12) United States Patent
Bradley et al.

(10) Patent No.: US 8,303,173 B2
(45) Date of Patent: Nov. 6, 2012

(54) DUAL POTTING TEMPERATURE PROBE

(75) Inventors: Keith J. Bradley, Atlanta, GA (US);
Ryan E. Johnson, Dawsonville, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 569 days.

(21) Appl. No.: 11/927,020

(22) Filed: Oct. 29, 2007

(65) Prior Publication Data
US 2009/0110029 A1 Apr. 30, 2009

(51) Int. Cl.
G01K 1/16 (2006.01)
G01K 7/22 (2006.01)
A61B 5/01 (2006.01)

(52) U.S. Cl. ........ 374/141; 374/163; 374/185; 374/208; 338/22 R; 600/549; 600/537

(58) Field of Classification Search .............. 374/100, 374/163, 166, 137, 110, 111, 112, 115, 178, 374/183, 185, 208, 141, 147, 148, 167, 4, 374/5, 43–45; 73/866.5; 338/28, 22 R; 392/441, 392/445; 128/203.17, 204.17
See application file for complete search history.

(56) References Cited

U.S. PATENT DOCUMENTS

| 3,402,378 | A | * | 9/1968 | Shew et al. ................ 338/28 |
| 3,593,704 | A | | 7/1971 | Schwab |
| 3,678,751 | A | | 7/1972 | Mead et al. |
| 3,713,899 | A | * | 1/1973 | Sebestyen .................. 136/233 |
| 3,738,173 | A | | 6/1973 | Sato |
| 3,845,706 | A | * | 11/1974 | Strimple et al. ............. 136/232 |
| 4,098,662 | A | * | 7/1978 | Schell et al. ................. 204/404 |
| 4,138,655 | A | * | 2/1979 | Nakano et al. ................. 338/30 |
| 4,138,878 | A | * | 2/1979 | Holmes et al. .................. 374/7 |
| 4,183,248 | A | | 1/1980 | West |
| 4,464,981 | A | * | 8/1984 | Stover ............................ 99/280 |
| 4,654,623 | A | * | 3/1987 | Steinschulte .................. 338/28 |
| 4,729,672 | A | * | 3/1988 | Takagi ......................... 374/208 |
| 4,750,497 | A | * | 6/1988 | Suzuki et al. ................. 600/549 |
| 4,934,831 | A | * | 6/1990 | Volbrecht ..................... 374/183 |

(Continued)

FOREIGN PATENT DOCUMENTS
JP 55039006 A * 3/1980
(Continued)

OTHER PUBLICATIONS
Manual for Fisher & Paykel Model Nos. MR700, MR720, MR730 Respiratory Humidifiers (Mar. 1998) (48 pages).
(Continued)

Primary Examiner — Gail Verbitsky
(74) Attorney, Agent, or Firm — Wood, Herron & Evans, LLP

(57) ABSTRACT

A temperature probe, such as for a respiratory system in which breathable gases are supplied to a patient, includes a housing having an external wall and an internal cavity defining an end and an internal cavity and further includes a temperature-responsive device in an area of the cavity near the end, such as in thermal communication with the external wall. A first potting compound that is deformable and/or has a relatively high thermal conductivity holds the temperature-responsive device in the cavity and a second potting compound having a relatively low thermal conductivity may be in the cavity behind the first potting compound. The housing may be made thin to enhance thermal conductivity, at least in the area containing the temperature-responsive device.

24 Claims, 2 Drawing Sheets

U.S. PATENT DOCUMENTS

| | | | |
|---|---|---|---|
| 5,165,798 A * | 11/1992 | Watanabe | 374/208 |
| 5,178,468 A * | 1/1993 | Shiokawa et al. | 374/185 |
| 5,348,397 A | 9/1994 | Ferrari | |
| 5,349,946 A * | 9/1994 | McComb | 128/203.17 |
| 5,367,604 A | 11/1994 | Murray | |
| 5,392,770 A | 2/1995 | Clawson et al. | |
| 5,667,306 A | 9/1997 | Montreuil et al. | |
| 5,743,646 A * | 4/1998 | O'Connell et al. | 374/148 |
| 5,749,656 A * | 5/1998 | Boehm et al. | 374/185 |
| 5,943,473 A | 8/1999 | Levine | |
| 6,078,730 A | 6/2000 | Huddart et al. | |
| 6,102,565 A * | 8/2000 | Kita et al. | 374/179 |
| 6,272,933 B1 | 8/2001 | Gradon et al. | |
| 6,349,722 B1 | 2/2002 | Gradon et al. | |
| 6,380,840 B1 * | 4/2002 | Wienand et al. | 338/25 |
| 6,584,972 B2 | 7/2003 | McPhee | |
| 6,676,290 B1 * | 1/2004 | Lu | 374/163 |
| 6,694,974 B1 | 2/2004 | George-Gradon et al. | |
| 6,802,314 B2 | 10/2004 | McPhee | |
| 6,918,696 B2 * | 7/2005 | Hoshisashi et al. | 374/208 |
| 6,988,497 B2 | 1/2006 | Levine | |
| 7,026,909 B2 * | 4/2006 | Glozman et al. | 338/28 |
| 7,147,369 B2 * | 12/2006 | Gadonniex et al. | 374/208 |
| 7,410,290 B2 * | 8/2008 | Tanaka | 374/121 |
| 7,458,718 B2 * | 12/2008 | Krishnamurthy et al. | 374/208 |
| 7,494,274 B2 * | 2/2009 | Sisk et al. | 374/185 |
| 7,553,078 B2 * | 6/2009 | Hanzawa et al. | 374/185 |
| 7,740,403 B2 * | 6/2010 | Irrgang et al. | 374/185 |
| 7,775,709 B2 * | 8/2010 | Biscotti et al. | 374/141 |
| 7,915,567 B2 * | 3/2011 | Lhuillier | 219/545 |
| 7,969,278 B2 * | 6/2011 | Kato et al. | 338/22 R |
| 7,982,580 B2 * | 7/2011 | Weber et al. | 338/28 |
| 2002/0129815 A1 | 9/2002 | McPhee | |
| 2002/0139367 A1 | 10/2002 | McPhee | |
| 2004/0060558 A1 | 4/2004 | Gradon et al. | |
| 2004/0079370 A1 | 4/2004 | Gradon et al. | |
| 2004/0141545 A1 * | 7/2004 | Hoshisashi et al. | 374/208 |
| 2005/0267382 A1 | 12/2005 | Church et al. | |
| 2006/0137445 A1 | 6/2006 | Smith et al. | |
| 2007/0237205 A1 * | 10/2007 | Hayashi | 374/163 |
| 2008/0025372 A1 * | 1/2008 | Culbertson et al. | 374/185 |
| 2008/0054497 A1 | 3/2008 | Bradley et al. | |
| 2008/0054500 A1 | 3/2008 | Bradley et al. | |
| 2008/0080592 A1 * | 4/2008 | Houben et al. | 374/185 |
| 2012/0063488 A1 * | 3/2012 | Nakayama et al. | 374/185 |

FOREIGN PATENT DOCUMENTS

| | | | |
|---|---|---|---|
| JP | 60219526 A * | 11/1985 | |
| JP | 03118432 A * | 5/1991 | |
| JP | 10221176 A * | 8/1998 | |
| JP | 2001242016 A * | 9/2001 | |

OTHER PUBLICATIONS

Technical Manual Fisher & Paykel Respiratory Humidifier Model Nos. MR700, MR720, MR730, MR 480 (Mar. 2001) (64 pages).

Allegiance Healthcare 510K No. K993833 for Airlife® Heated Ventilator and Anesthesia Breathing Circuits (5 pages) (Dec. 10, 1999).

Brochure for Hudson RCI Humid-Heat® (6 pages).

Operating Manual for Fisher & Paykel Model Nos. MR700, MR720, MR730 Respiratory Humidifiers (Mar. 1994) (46 pages).

Instruction Sheet for Airlife® Single Heated Adult Respiratory Circuit (2 pages) (date uncertain).

Cardinal Health RT110 Data for Circuits, reprinted from the internet Jun. 3, 2006 (2 pages).

Fisher & Paykel 900MR561 Temperature Probe Label (one page) (date uncertain).

Fisher & Paykel Airway Temperature Probes Instructions for Use (3 pages) (2003).

Cat. RT110 Insert for Airlife™ Adult Respiratory Circuit—Heated (one page) (undated).

Official Action in related U.S. Appl. No. 11/927,077 mailed Feb. 2, 2011 (9 pages).

Official Action in related U.S. Appl. No. 11/927,077 mailed Jul. 7, 2011 (9 pages).

* cited by examiner

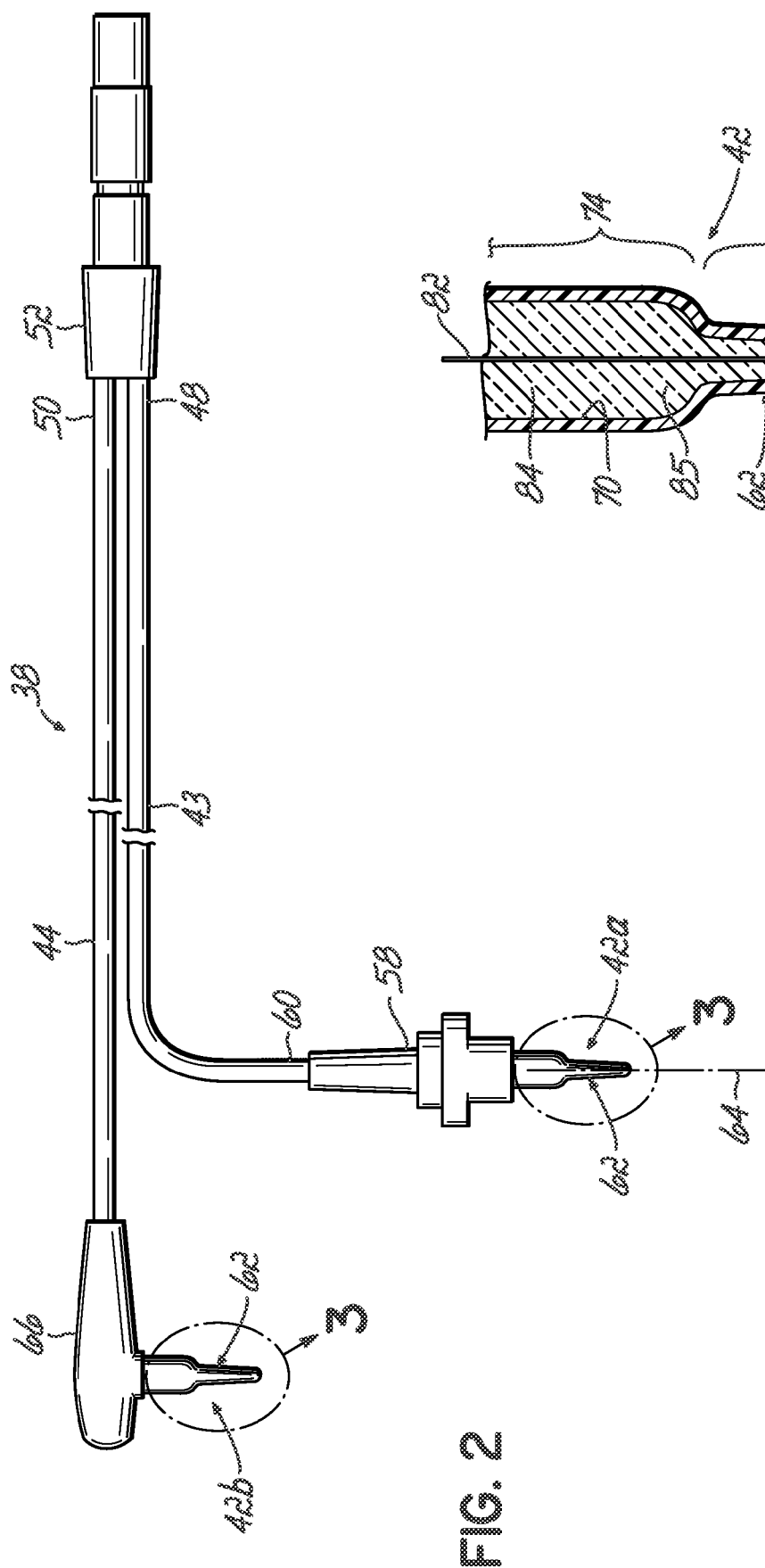
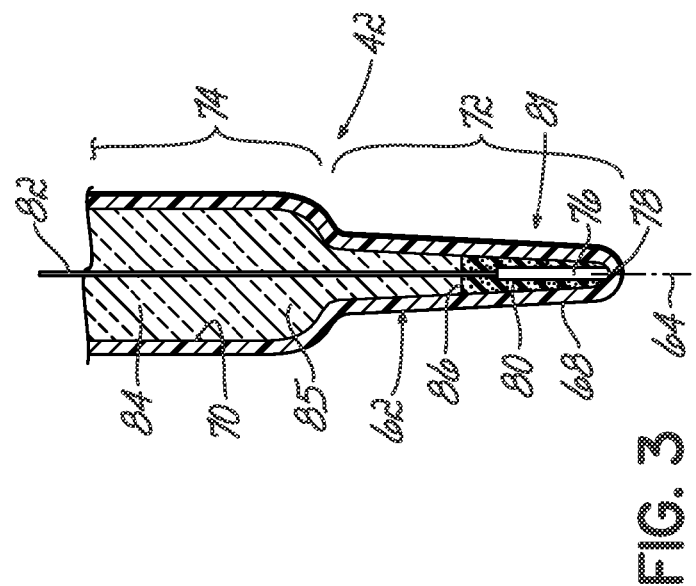
FIG. 2
FIG. 3

DUAL POTTING TEMPERATURE PROBE

FIELD OF THE INVENTION

The present invention relates generally to respiratory systems incorporating a humidification system, and more particularly, to a temperature probe for sensing the temperature of a breathable gas at desired locations in such a respiratory system.

BACKGROUND OF THE INVENTION

Respiratory systems provide breathable gas, such as oxygen, anesthetic gas, and/or air directly to a patient's mouth, nose, or airway to assist or facilitate breathing by the patient. A ventilator may be used as part of the respiratory system to drive the breathable gas to the patient through an inspiratory limb hose or conduit. An expiratory limb hose or conduit may be provided to allow air to expel from the patient.

It is typically desired to warm and impart humidity to the breathable gas before it is provided to the patient. For that purpose, many respiratory systems include a humidification system having a chamber for holding water and a heater unit including a heater adapted to heat the chamber. The chamber may be manually refillable, or there may be a water source to selectively fill the chamber as it empties. The breathable gas is passed through the chamber to be heated and humidified. An example of a heater unit and chamber arrangement is shown in U.S. Pat. Nos. 6,988,497 and 5,943,473. The inspiratory limb carries the heated and humidified gas to the patient and the expiratory limb, if present, carries exhaled air and possibly other gases from the patient. The inspiratory and/or expiratory limbs may also be heated such as by heater circuits comprised of one or more elongated wires running along the limb, such as through the interior thereof. An example of a breathing circuit with heated limbs is shown in U.S. Pat. No. 6,078,730.

Maintaining the desired temperature of gas(es) passing through this type of respiratory system may require adjusting the temperature of the heater in the heater unit and/or the heater circuits in the inspiratory and expiratory limbs in response to thermal feedback from the system. Thus, some respiratory systems include temperature probes at one or more locations, such as for sensing the temperature of the heated and humidified gas supplied to the patient. The temperature probes may be operatively coupled to the heater unit, which then adjusts the power levels to the heater and/or heater circuit(s) based at least in part on the measured temperatures. Current temperature probes for respiratory systems typically include a temperature-responsive device, such as a thermistor or other resistance temperature detector (RTD), within a protective housing. More specifically, the thermistor, which is typically held by epoxy within a cylindrical container, is typically inserted into an internal cavity of the housing and placed in thermal communication with an exterior wall at an end of the housing. Lead wires are electrically coupled to and extend away from the thermistor to be electrically coupled to an associated temperature cable at an opposite end of the housing for electrically communicating with the heater unit.

To hold or stabilize the thermistor within the internal cavity of the housing, an amount of potting compound is typically placed into the housing around the thermistor and lead wires, and then cured to encapsulate substantial portions of the thermistor and lead wires. But the nature of the typical potting compound and/or housing limits response time of the probe to transient or time-varying thermal conditions, and can present other drawbacks.

SUMMARY OF THE INVENTION

The present invention provides a temperature probe for use in a respiratory system with improved thermal response time and which can overcome other drawbacks of prior temperature probes. To that end and in accordance with the principles of the present invention, the area near the tip of the probe housing containing the temperature-responsive device is provided with a first potting compound having relatively high thermal conductivity, and the area of the housing spaced therebehind is provided with a second potting compound having a relatively low thermal conductivity. By contrast, typical of prior probes is that each probe was understood to include only one potting compound and it had a relatively low thermal conductivity. As a result, in prior probes, the potting compound tended to serve as an insulator thereby slowing thermal response time of the probe. With the probe of the present invention, thermal response time of the probe is enhanced (i.e., the probe responds more quickly to changes in thermal conditions). The first compound enhances heat transfer to the temperature-responsive device and the second potting compound provides an insulative layer to reduce heat leakage from the area adjacent the temperature-responsive device.

Additionally, or alternatively, in accordance with another aspect of the invention, the probe housing may be formed from a relatively high thermal conductivity material and configured to have a reduced wall thickness at least in the region containing the temperature-responsive device. Both of these aspects enhance heat transfer to the temperature-responsive device, which enables the device to more quickly react to temperature changes in the surrounding gas. By contrast, the housings of prior probes were understood to typically have relatively thick walls throughout, and especially in the area of the temperature-responsive device, and to be of material that was also of relatively low thermal conductivity, thus tending to reduce thermal responsiveness of the probe.

In yet another aspect of the invention, at least the first potting compound may be a material that is relatively compliant so as to readily deform under applied stresses. Such a material effectively dampens any stresses from being transferred to the temperature-responsive device, such as those that occur during accidental bumps or drops. The resulting temperature probe is thus more robust and durable.

By virtue of the foregoing, there is provided a temperature probe for use in a respiratory system with improved thermal response time and which can overcome other drawbacks of prior temperature probes. These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate an embodiment of the invention and, together with a general description of the invention given above, and the detailed description given below, serve to explain the invention.

FIG. 2 is an enlarged side elevation view of the patient temperature cable of FIG. 1; and FIG. 3 is an enlarged cross-sectional view of the temperature probes used in the patient temperature cable of FIG. 2 and taken from encircled area 3 in FIG. 2.

DETAILED DESCRIPTION OF THE DRAWINGS

Figure 1:
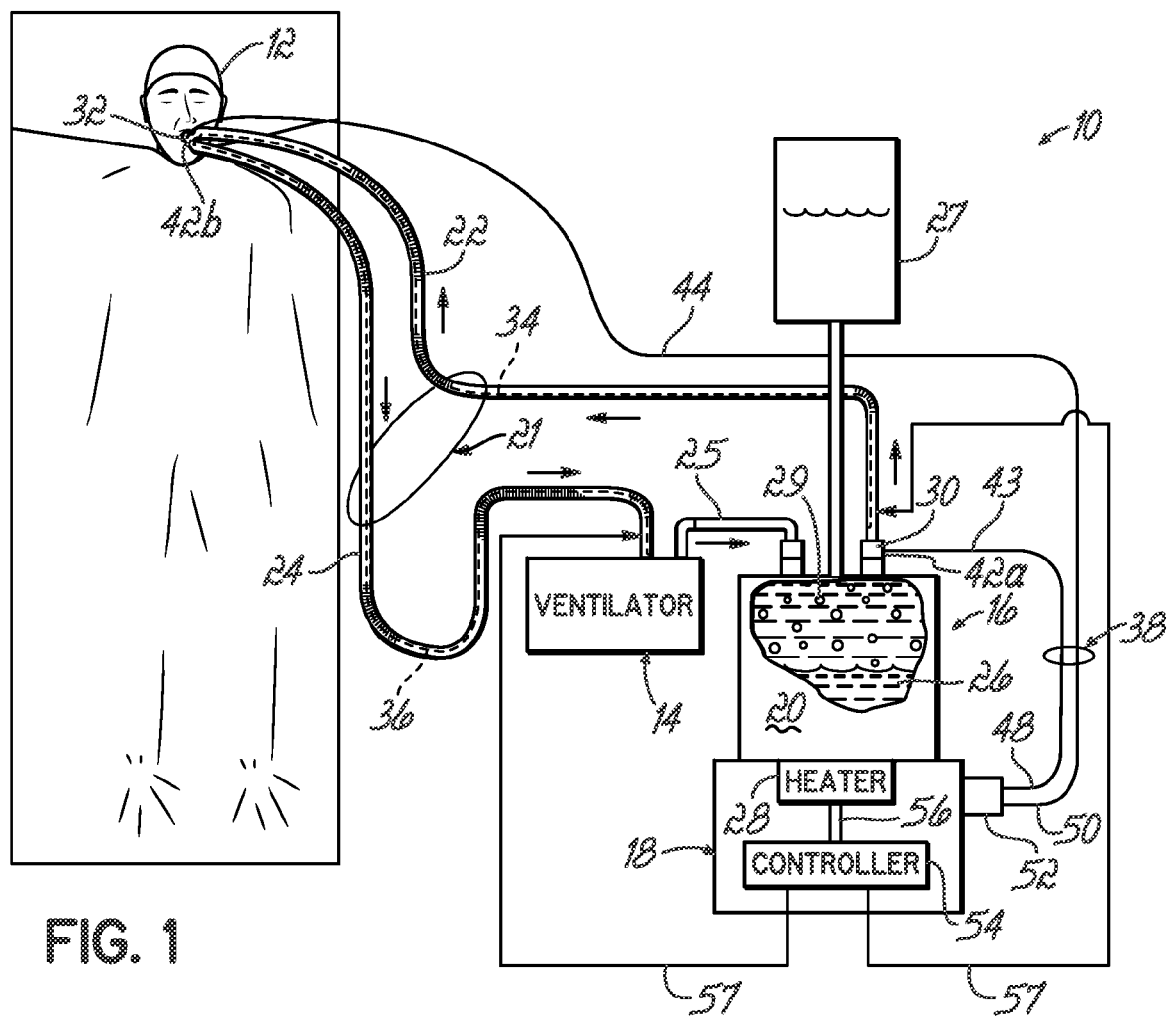
FIG. 1 is a schematic illustration of an exemplary respiratory system including a patient temperature cable including temperature probes constructed in accordance with the principles of the present invention.

FIG. 1 is an exemplary respiratory system 10 for supplying breathable gases to a patient 12. In the illustrated embodiment, the respiratory system 10 includes a ventilator 14, a humidification system 16 having a heater unit 18, a heatable container for water such as a disposable chamber 20, and a breathing circuit 21 having a first elongated hose or conduit 22 defining an inspiratory limb 22 and second elongated hose or conduit 24 defining an expiratory limb. Ventilator 14 drives breathable gas, such as oxygen, anesthetic gas and/or air, through gas conduit 25 and into an inlet of chamber 20. Water 26 is received in chamber 20, either by being poured in manually or automatically from a water supply 27 such as a bag or bottle, which may be vented. Chamber 20 is heated by a heater 28, such as hot plate and one or more heating elements, (not shown), of heater unit 18 to heat up the water 26 therein. Heated water vapor 29 may also be produced within chamber 20 above the level of water 26 therein. The gas from conduit 25 passes over or through the heated water 26 and/or through heated water vapor 29 to become heated and humidified before exiting the chamber 20 as heated and humidified gas. Examples of humidification systems are shown in aforementioned U.S. Pat. Nos. 6,988,497 and 5,943,473, and co-pending U.S. patent application Ser. No. 11/469,086 filed Aug. 31, 2006 and Ser. No. 11/469,113 filed Aug. 31, 2006, the disclosures of all four of which are incorporated herein by reference in their entireties.

The heated and humidified gas flows from chamber 20 to the patient 12 through inspiratory limb 22. To this end, a first end of inspiratory limb 22 is coupled to chamber 20 by a connecting member or joint 30, and a second end of inspiratory limb 22 is coupled to a breathing attachment 32 that facilitates delivery of the gas passed therethrough to patient 12. The breathing attachment 32 may couple to an invasive apparatus such as an endotrachael tube, or a non-invasive apparatus such as a mask that promotes gas delivery. If desired, the gas may be further heated while passing through inspiratory limb 22 to breathing attachment 32 by providing a heating circuit 34 associated with inspiratory limb 22. Another heating circuit 36 may be associated with expiratory limb 24, which allows exhaled air and other gas expelled from patient 12 to pass back to ventilator 14, the atmosphere or elsewhere.

Respiratory system 10 also includes a patient temperature cable (PTC) 38 having one or more temperature probes 42 (two shown in FIG. 2 as 42a and 42b, respectively) to provide thermal feedback to heater unit 18. The feedback received from the probes enable heater unit 18 to vary the power levels to heater 28 and/or heater circuits 34, 36 in order to regulate the temperature of the gas supplied to the patient 12 at a pre-selected temperature set point conducive to proper respiration and lung viability.

As shown in FIGS. 1 and 2, in one exemplary embodiment patient temperature cable 38 includes a first communication cable 43 having a first temperature probe 42a coupled thereto and a second communication cable 44 having a second temperature probe 42b coupled thereto. First temperature probe 42a may be partially inserted through an opening (not shown) in connecting member 30 and positioned so as to be in thermal communication with the inspiratory gas flowing through inspiratory limb 22, such as in the flow path thereof. Alternatively, probe 42a may be positioned adjacent the flow path of inspiratory limb 22, but in thermal communication with the gas flowing therethrough. First temperature probe 42a is responsive to the temperature of the gas exiting chamber 20 and is electrically coupled to heater unit 18 by first communication cable 43, which has an end 48 electrically coupled to heater unit 18.

Similarly, second temperature probe 42b may be partially inserted through breathing attachment 32 and positioned so as to be in thermal communication with the inspiratory gas flowing through attachment 32 and into patient 12. Second temperature probe 42b may be located directly in the gas flow path of attachment 32 or adjacent the flow path, but in thermal communication with the gas flowing therethrough. Second temperature probe 42b is electrically coupled to heater unit 18 by second communication cable 44, which also has an end 50 electrically coupled to heater unit 18. Ends 48 and 50 may be advantageously secured together by a connector 52 to facilitate coupling the first and second cables 43, 44 to a mating socket (not shown) on heater unit 18.

A controller 54 in heater unit 18 is operatively associated with heater 28 as at 56 (and with heater circuits 34, 36 as at 57) and adapted to control energization of heater 28 (and heater circuits 34, 36 in inspiratory and expiratory limbs 22, 24, respectively) in order to desirably heat water 26 so as to create water vapor 29 by which to heat and humidify the breathable gas passing through chamber 20. A microprocessor or logic circuit (not shown) within controller 54 processes the information from temperature probe(s) 42 to determine whether any adjustments need to be made to the power supplied to heater 26 (or heater circuits 34 and 36). Various details of a controller 54 and associated control logic for adjusting the power supplied to heater 26 and/or heater circuits 34, 36 are provided in the following concurrently-filed U.S. patent applications: U.S. patent application Ser. No. 11/926,990; U.S. patent application Ser. No. 11/927,000; U.S. patent application Ser. No. 11/927,004; U.S. patent application Ser. No. 11/927,013; U.S. patent application Ser. No. 11,927,054; and U.S. patent application Ser. No. 11/927,068. All of the above-mentioned concurrently-filed U.S. patent applications are incorporated herein by reference in their respective entireties.

FIG. 2 illustrates the patient temperature cable 38 in further detail. First temperature probe 42a may be coupled to first communication cable 43 by an overmold 58. More specifically, an end portion 60 of first communication cable 43 is typically inserted into the first temperature probe 42a and secured to an outer housing 62 (FIG. 3) by a conventional fastener, such as a cable tie (not shown). To reinforce the connection, overmold 58 may be molded over end portion 60 and at least a proximal portion of outer housing 62. The end portion 60 and first temperature probe 42a may be coupled substantially along an axis 64 so that patient temperature cable 38 may be properly positioned in the respiratory system 10.

Similarly, second temperature probe 42b may be coupled to second communication cable 44 by an overmold 66. Second temperature probe 42b has the same general design as first temperature probe 42a, as will be described in greater detail below. Due to its particular location in the respiratory system 10, however, second temperature probe 42b may be arranged perpendicularly with respect to second communication cable 44. Thus, the portion of second communication cable 44 inserted into or immediately proximate housing 62, including a right-angle bend and overmold 66, may be configured to accommodate the particular orientation of second temperature probe 42b with respect to second communication cable 44.

Overmolds 58 and 66 provide strain relief so that communication cables 40 and 44 do not separate from their respective temperature probes 42 when the cables are bent or placed in tension. In one embodiment, overmolds 58 and 66 are formed from a thermoplastic resin, such as Santoprene TPV 8281-90MED, and have a durometer of approximately 90 Shore A. The shape and materials of the overmolds 58 and 66 may be selected to serve ergonomic functions as well, making the patient temperature cable 38 easier to grip and temperature probes 42 easier to handle. Furthermore, overmolds 58 and 66 may be designed to act as a moisture barrier to protect wires and other internal components of temperature probes 42 from damage.

FIG. 3 is a cross sectional view of the temperature probes 42 for purposes of explaining in further details the features of the present invention. First and second temperature probes 42a and 42b are substantially identical for purposes of the present invention, so only one need be described in detail. To that end, temperature probe 42 includes an outer housing 62 having an external wall 68 and an internal cavity 70 with a first region 72 and a second region 74. At least a portion of first region 72 is smaller than at least a portion of second region 74 such that housing 62 is provided with two different cavity sizes. For example, in one embodiment, first region 72 of cavity 70 has a cross dimension (e.g., diameter) less than a cross dimension of second region 74 and may further include a slight taper.

A temperature-responsive device 76, which may include a thermistor, thermocouple, or other resistance temperature detector (RTD), may be positioned within internal cavity 70 of outer housing 62. Advantageously, if temperature responsive device 76 includes a thermistor, the thermistor is secured within a cylindrical container with epoxy (not shown) before being placed into outer housing 62. More specifically, temperature-responsive device 76 may be closely received in the first region 72 and in thermal communication with external wall 68 adjacent an end or tip 78 of cavity 70. The temperature-responsive device 76 is held or stabilized within first region 72 by a first potting compound 80 deposited in internal cavity 70, which at least partially encapsulates, and may advantageously substantially completely encapsulate, temperature-responsive device 76 in cavity 70 in the area 81 of region 72 near the tip 78. Lead wires 82 (only one shown) electrically coupled to temperature-responsive device 76 extend from first region 72, through the second region 74, and ultimately to communication cable 43 or 44, to which they are electrically coupled. A second potting compound 84 is deposited in second region 74 in an area 85 of region 72 and/or 74 behind first potting compound 80 and may at least partially encapsulate lead wires 82 in cavity 70 and may further extend into region 72 towards area 81. The first and second potting compounds may be in adjoining relationship such that they meet along a distinct interface as at 86 in FIG. 3 or merge through a non-distinct area (not shown). There may be gaps in the interface or merge, however. Alternatively, the two potting compounds may not be in adjoining relationship such that they do not contact but are instead spaced apart within cavity 70, such as by an air pocket or void therebetween (not shown).

In an advantageous aspect of the invention, the first and second potting compounds 80, 84, may be selectively chosen to improve the thermal response time of temperature probe 42 while also minimizing thermal load losses that may effect the readings of probe 42. For example, first potting compound 80 may be selected from a material that has a relatively high thermal conductivity, which facilitates heat transfer, while second potting compound 84 may be selected from a material that has a relatively low thermal conductivity, which reduces or diminishes heat transfer. The relatively high thermal conductivity of first potting compound 80 allows thermal changes adjacent external wall 68, such as in the gas flowing through inspiratory limb 22, to be readily transferred through the first potting compound 80 and to the temperature-responsive device 76. Because the resistance to heat transfer through the potting compound 80 is reduced as compared to prior temperature probes, the time it takes the temperature-responsive device 76 to sense a change in the temperature of the gas is correspondingly reduced. Thus, response times are decreased, resulting in a temperature probe that can more quickly respond to temperature changes in the surrounding gas.

In a similar manner, the relatively low thermal conductivity of second potting compound 84 creates an insulative barrier adjacent to, and possibly extending into, first region 72 toward area 81 containing temperature-responsive device 76. The low thermal conductivity of second potting compound 84 minimizes thermal load losses up through the probe housing, and effectively, concentrates the thermal energy of the surrounding gas along the first region 72, where it may be readily sensed by the temperature-responsive device 76.

By way of example, in one exemplary embodiment, first potting compound 80 may have a thermal conductivity greater than approximately 10 BTU/hr/ft$^2$/° F./in and second potting compound 84 may have a thermal conductivity less than approximately 1 BTU/hr/ft$^2$/° F./in. More specifically, first potting compound 80 may be an epoxy resin having a thermal conductivity of approximately 12 BTU/hr/ft$^2$/° F./in (such as 50-3170 Resin available from Epoxies Etc.) and second potting compound 84 may be an insulating, urethane-foaming resin having a thermal conductivity of approximately 0.3 BTU/hr/ft$^2$/° F./in (such as 20-2028 Foam from Epoxies Etc.).

Outer housing 62 may also be configured to improve heat transfer from external wall 68 to temperature-responsive device 76. For example, outer housing 62 may be molded from a plastic material that has a relatively high thermal conductivity, such as greater than the thermal conductivity of potting compound 84. The high thermal conductivity of outer housing 68 minimizes the resistance to heat transfer so that thermal changes in the gases are readily transferred through the housing and to the temperature-responsive device 76. Thus, in a similar manner as above for the first potting compound 80, the increased thermal conductivity of the outer housing 62 decreases the probe's response time, resulting in a temperature probe that can more quickly respond to temperature changes in the surrounding gas. Additionally, the thickness of outer housing 62 may be advantageously reduced so as to further minimize the resistance to heat transfer through housing 62 and further decrease the probe's response time.

In addition to the above, the material for outer housing 62 preferably satisfies other design criteria. For example, the outer housing 62 may advantageously be made of a material having a relatively low electrical conductivity to effectively electrically insulate the temperature-responsive device 76. The outer housing material may also advantageously have excellent chemical resistance and provide for high dimensional accuracy for manufacturing purposes. For example, in one embodiment, outer housing 62 may be approximately 0.02 inches thick, at least in area 81 if not all of region 72 (and possibly region 74 if desired), and molded from a thermoplastic resin reinforced with glass fibers, such as Udel® GF-120 or a similar polysulfone resin available from Solvay Corporation.

In a further aspect of the invention, first potting compound 80 may be selected from a material that improves the durability of the temperature probe 42. As is known in the art, many current temperature probes are fragile in that accidental drops or bumps often result in the temperature-responsive device 76 breaking or malfunctioning. To minimize the mechanical stresses transferred to temperature-responsive device 76 whenever the probe is dropped, bumped, transported, or otherwise handled, first potting compound 80 may advantageously be formed from a material having a relatively low durometer so as to be compliant or flexible, even after being cured to encapsulate and hold device 76 within housing 62. For instance, a material having a durometer of 90 Shore A may be used. A material of this low durometer flexes or deforms when mechanical stresses are applied. In essence, the compliance or ability of first potting compound 80 to deform dampens mechanical stresses acting on the temperature-responsive device 76. This in turn not only minimizes breakage of the temperature-responsive device 76, but may also minimize the effects of stress on the temperature-responsive device 76 to provide a more accurate temperature measurement.

In use, temperature probes 42 of patient temperature cable 38 are located in respiratory system 10 as described above and cable 38 is coupled to heater unit 18. Temperature probes 42 are in thermal communication with the heated and humidified gas flowing through inspiratory limb 22 and communicate temperature information of the gas to heater unit 18. Due to the particular construction of temperature probes 42, the probes are capable of quickly responding to thermal changes in the gas. Accordingly, heater unit 18 may quickly adjust the temperature of heater 26 and/or heater circuits 34, 36 so as to maintain a temperature-set point. To benefit from the improved response time of the temperature probes 42, heater 26 may be constructed so as to have a similar response time, i.e., heater 26 is capable of quickly heating up or cooling down. One such heater 26 capable of utilizing the improved response time of the temperature probes 42 is disclosed in concurrently filed U.S. patent application Ser. No. 11/926,982, which is incorporated by reference herein in its entirety. The improved response time of both the temperature probes and heater provide enhanced control over the heating and humidification of the breathable gas(es) to maintain a close tolerance to the pre-selected set point conditions that constitutes a considerable improvement over the set point tolerances achieved in prior respiratory systems.

By virtue of the foregoing, there is provided a temperature probe for use in a respiratory system with improved thermal response time and which can overcome other drawbacks of prior temperature probes.

While the present invention has been illustrated by a description of an embodiment thereof and specific examples, and while the embodiment has been described in some detail, it is not intended to restrict or in any way limit the scope of the appended claims to such detail. Additional advantages and modifications will readily appear to those skilled in the art. For example, while cable 38 has been shown having two cables 43 and 44 coupled to respective first and second probes 42a and 42b, it will be appreciated that cable 38 might have only one of cables 43 or 44 and its associated probe 42. Additionally, while first potting compound 80 is shown and described as a continuous resinous compound, the compound may contain some amount of voids, bubbles, etc. and still provide a highly thermally conductive path from the external wall to the temperature-responsive device. Moreover, only one potting compound, such as compound 80 and being deformable, might be included in some embodiments. Still further, it will be appreciated that while temperature probes 42 have been described in the context of a respiratory system having a humidification system, the temperature probe of the present invention may be utilized in a wide variety of applications for which it is desired to measure temperature. The invention in its broader aspects is therefore not limited to the specific details, representative apparatus and methods and illustrative examples shown and described. Accordingly, departures may be made from such details without departing from the scope or spirit of the general inventive concept.

Having described the invention, what is claimed is:

1. A respiratory system comprising:
a heater adapted to heat a container of water through which gas passes and becomes heated and humidified;
a controller operatively coupled to the heater; and
a temperature probe operatively coupled to the controller, the temperature probe comprising:
a housing having an external wall defining a closed end made of thermoplastic resin and an internal cavity, a distal aspect of the internal cavity being surrounded by the thermoplastic resin closed end;
a temperature-responsive device positioned in an area within the distal aspect of the internal cavity;
a first potting compound in the area holding the temperature-responsive device therein, the first potting compound touching the thermoplastic resin closed end thereat and having a first thermal conductivity; and
a second potting compound in an area of the cavity defining a proximal aspect of the internal cavity behind the first potting compound, the second potting compound having a second thermal conductivity lower than the first thermal conductivity,
wherein the temperature probe is adapted to sense the temperature of the humidified gas and the controller is adapted to control output of the heater based on the sensed temperature from the temperature probe.

2. The respiratory system of claim 1, wherein the temperature-responsive device is in thermal communication with the external wall of the housing.

3. The respiratory system of claim 1, further comprising:
a second temperature probe operatively coupled to the controller and adapted to sense the temperature of the humidified gas.

4. A temperature probe assembly comprising:
a first cable and a first temperature probe,
the first temperature probe comprising:
a housing having an external wall defining a closed end made of thermoplastic resin and an internal cavity, a distal aspect of the internal cavity being surrounded by the thermoplastic resin closed end;
a temperature-responsive device positioned in an area within the distal aspect of the internal cavity;
a first potting compound in the area holding the temperature-responsive device therein, the first potting compound touching the thermoplastic resin closed end thereat and having a first thermal conductivity; and
a second potting compound in an area of the cavity defining a proximal aspect of the internal cavity behind the first potting compound, the second potting compound having a second thermal conductivity lower than the first thermal conductivity, and the first cable having a first end including a connector adapted to be coupled to a mating socket, the first temperature probe being operatively coupled to a second end of the first cable.

5. The temperature probe assembly of claim 4, the temperature-responsive device of the temperature probe including a thermistor.

6. The temperature probe assembly of claim 4, further comprising:
a second temperature probe; and
a second cable having a first end coupled to the connector adapted to be coupled to the mating socket, the second temperature probe being operatively coupled to a second end of the second cable.

7. The temperature probe assembly of claim 6, the first temperature probe being coupled to the first cable along an axis thereof and the second temperature probe being coupled to the second cable perpendicularly thereto.

8. A temperature probe comprising:
a housing having an external wall defining a closed end made of thermoplastic resin and an internal cavity, a distal aspect of the internal cavity being surrounded by the thermoplastic resin closed end;
a temperature-responsive device positioned in an area within the distal aspect of the internal cavity;
a first potting compound in the area holding the temperature-responsive device therein, the first potting compound touching the thermoplastic resin closed end thereat and having a first thermal conductivity; and
a second potting compound in an area of the cavity defining a proximal aspect of the internal cavity behind the first potting compound, the second potting compound having a second thermal conductivity lower than the first thermal conductivity.

9. The temperature probe of claim 8, the cavity defining a first region adjacent the closed end and containing the area holding the temperature responsive device and defining a second region proximate to the first region, the first region having a first cross dimension and the second region having a second cross-dimension greater than the first cross dimension.

10. The temperature probe of claim 8, the temperature-responsive device being in thermal communication with the external wall of the housing.

11. The temperature probe of claim 10, the external wall of the housing having a thermal conductivity greater than the second thermal conductivity.

12. The temperature probe of claim 8, the temperature-responsive device including a thermistor.

13. The temperature probe of claim 8, the first potting compound having a thermal conductivity greater than approximately 10 BTU/hr/ft$^2$/° F/in.

14. The temperature probe of claim 8, the second potting compound having a thermal conductivity less than approximately 1 BTU/hr/ft$^2$/° F./in.

15. The temperature probe of claim 8, the first potting compound being deformable.

16. The temperature probe of claim 8, the first potting compound having a durometer of approximately 90 Shore A.

17. The temperature probe of claim 8, the first and second potting compounds being in adjoining relationship.

18. The temperature probe of claim 8, the temperature-responsive device substantially completely encapsulated in the first potting compound.

19. The temperature probe of claim 8 further including lead wires electrically coupled to the temperature-responsive device.

20. The temperature probe of claim 8, the external wall having a thickness of about 0.02 inches in the area containing the temperature responsive device.

21. The temperature probe of claim 8, the first and second potting compounds being resins.

22. The temperature probe of claim 21, the first potting compound being an adhesive resin.

23. The temperature probe of claim 22, the second potting compound being an insulating, urethane-foamed resin.

24. The temperature probe of claim 21, the second potting compound being an insulating, urethane-foamed resin.

* * * * *